United States Patent [19]

Martin

[11] 4,208,503
[45] Jun. 17, 1980

[54] EPOXY-FUNCTIONAL POLYSILOXANE POLYMERS

[75] Inventor: Eugene R. Martin, Onsted, Mich.

[73] Assignee: SWS Silicones Corporation, Adrian, Mich.

[21] Appl. No.: 943,011

[22] Filed: Sep. 18, 1978

Related U.S. Application Data

[63] Continuation-in-part of Ser. No. 801,509, May 31, 1977, which is a continuation-in-part of Ser. No. 729,069, Oct. 4, 1976, abandoned, which is a continuation of Ser. No. 566,000, Apr. 7, 1975, abandoned.

[51] Int. Cl.$^2$ .............................................. C08G 77/06
[52] U.S. Cl. .................................... 528/14; 260/348.41; 528/12; 528/21; 528/27; 528/33; 528/34; 528/37
[58] Field of Search ................... 528/27, 33, 34, 14, 528/12, 21, 37; 260/348.41

[56] References Cited

U.S. PATENT DOCUMENTS

| | | | |
|---|---|---|---|
| 2,997,458 | 8/1961 | Lewis | 528/27 |
| 3,057,901 | 10/1962 | Plueddemann | 528/27 |
| 3,455,877 | 7/1969 | Plueddemann | 528/33 |
| 3,563,941 | 2/1971 | Plueddemann | 528/27 |
| 3,660,434 | 5/1972 | Patterson | 528/27 |
| 3,761,444 | 9/1973 | Mendicino | 528/27 |
| 4,082,726 | 4/1978 | Mine et al. | 528/33 |

Primary Examiner—Melvyn I. Marquis

[57] ABSTRACT

The invention relates to novel epoxy-functional polysiloxane polymers having the general formula

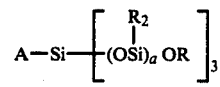

in which A is a radical containing at least one epoxy group, R is a monovalent hydrocarbon radical having up to 18 carbon atoms and a is a number of from 1 to 20,000. These novel polymers may be prepared by equilibrating silanes containing at least one epoxy group with an organopolysiloxane in the presence of a base catalyst.

11 Claims, No Drawings

EPOXY-FUNCTIONAL POLYSILOXANE POLYMERS

CROSS REFERENCE TO RELATED APPLICATIONS

This application is a continuation-in-part of application Ser. No. 801,509, filed May 31, 1977 which was a continuation-in-part of application Ser. No. 729,069 filed on Oct. 4, 1976 now abandoned, which was a continuation of application Ser. No. 566,000 filed on Apr. 7, 1975 and now abandoned.

BACKGROUND OF THE INVENTION

The present invention relates to organopolysiloxanes, and more particularly to epoxy-functional organopolysiloxanes and to a process for preparing the same.

Heretofore, epoxy containing organosilicon compounds have been prepared by reacting an organopolysiloxane with a dialkali metal salt and thereafter reacting the resultant product with an epihalohydrin. (See U.S. Pat. No. 2,997,458 to Lewis.) Also, U.S. Pat. No. 3,660,434 to Patterson discloses reacting aminosilanes with silanols having terminal double bonds and thereafter reacting the resultant product with epoxide compounds. Organosilicon epoxides are also disclosed in U.S. Pat. No. 3,455,877 to Plueddemann in which these organosilicon epoxides are prepared by reacting organosilicon compounds containing a C=C group with peracids or by reacting an unsaturated organic compound containing at least one epoxy group with a silicon compound containing at least one SiH group in the presence of a platinum compound.

Also, U.S. Pat. No. 3,563,941 to Plueddemann discloses epoxy silicon compounds which are obtained by reacting a hydroxyl-terminated dimethylpolysiloxane with gamma-glycidoxypropyltrimethoxysilane to form silicon compounds having a methoxy group linked to the same silicon atom as the epoxy group, whereas in the polysiloxane polymers of this invention, the hydrocarbonoxy group is linked to a terminal silicon atom. Moreover, the hydrocarbonoxy group is linked to a different silicon atom than the epoxy group. Thus, the polysiloxane polymers of this invention are more resistant to hydrolysis than the epoxy silicon compounds described by Plueddemann.

Epoxy substituted siloxanes are described in U.S. Pat. No. 3,761,444 to Mendicino, in which lower molecular weight epoxy substituted siloxanes are equilibrated with other siloxanes in the presence of water, a silanol and a basic equilibration catalyst to form siloxane copolymers containing the substituents of both the epoxy siloxane and the other siloxanes.

Johnson et al disclose in U.S. Pat. No. 3,431,143 epoxy-silicones which are prepared by the platinum catalyzed addition of aliphatically unsaturated epoxy compounds to hydrosiloxanes. In contrast to Mendicino and Johnson et al, the polysiloxane polymers of the present invention are branched epoxy containing polysiloxanes.

U.S. Pat. No. 3,887,487 to Camp discloses organosilicon compounds having an oxirane radical bonded directly to a silicon atom which is obtained by the partial or complete hydrolysis of a silane containing an oxirane group and an alkoxy group with conventional silanes, followed by condensation and rearrangement. In the resulant compounds, the alkoxy group and the oxirane radical are bonded to the same silicon atom. In contrast to the copolymers described by Camp, the branched polysiloxane polymers of this invention are more stable to hydrolysis since the epoxy group and hydrocarbonoxy groups are linked to different silicon atoms.

The above described methods for preparing epoxy containing organosilicon compounds have several disadvantages. For example, if a monoepoxy-functional dimethylpolysiloxane composition is desired, the above described methods require a siloxane having a single amino-functional group or one SiH group, or a siloxane which contains one C=C group. Even though it is known that the aforementioned organofunctional siloxanes can be prepared by equilibration, condensation or cohydrolysis, each process leads to a random distribution of the functional groups. Thus, some of the molecules contain more than one organofunctional group, others contain one, and still others contain no functional groups. Therefore, conversion of the organofunctional group to an epoxide results in the same random distribution. Moreover, some of the methods described in the prior art do not produce epoxy-functional polysiloxane polymers which are resistant to hydrolysis.

Therefore, it is an object of this invention to provide a new class of epoxy-functional polysiloxane polymers. Another object of this invention is to provide a method for preparing branched epoxy-functional polysiloxanes. Still another object of this invention is to provide a method for preparing epoxy-functional polysiloxanes without first having to prepare aminosilanes, vinyl containing siloxanes or SiH containing siloxanes. A further object of this invention is to provide epoxy-functional polysiloxanes which are substantially free from SiH groups and are substantially more resistant to hydrolysis.

The foregoing objects and others which will become apparent from the following description are accomplished in accordance with this invention, generally speaking, by providing epoxy-functional polysiloxane polymers of the general formula

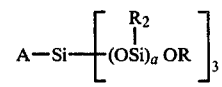

in which A is a radical containing at least one epoxy group, R is a monovalent hydrocarbon radical having up to 18 carbon atoms and a is a number of from 1 to 20,000.

DETAILED DESCRIPTION OF THE INVENTION

These epoxy-functional polysiloxane polymers are preferably prepared by equilibrating silanes containing at least one epoxy-functional group with cyclic organopolysiloxanes in the presence of a basic catalyst and an aprotic solvent, if desired.

Examples of suitable silanes which may be equilibrated with the cyclic organopolysiloxanes are epoxy-functional silanes of the formula

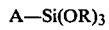

in which A is a radical which contains at least one epoxy group and may be represented by the general formula

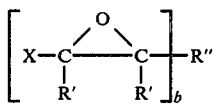

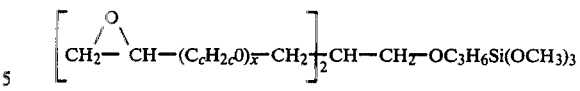

in which R is a monovalent hydrocarbon radical having from 1 to 18 carbon atoms, R' is hydrogen or R and when the R'(s) are hydrocarbon radicals, they can be taken together with the vicinal carbon atoms, to represent a cyclic group such as a cyclohexane ring or cyclopentane ring which may be unsubstituted or substituted with alkyl or aryl substituents, R" may represent a divalent, trivalent or tetravalent radical such as an alkylene radical, an arylene radical having up to 18 carbon atoms or an oxyalkylene, or oxyarylene radical containing C—O—C linkages, X represents hydrogen or a monovalent radical consisting of a single carbon atom or a group of carbon atoms interconnected by a single or multiple bond which contains additional groups such as hydrogen, alkyl, hydroxyl, alkoxy and cyclic hydrocarbons, and b is a number of from 1 to 3.

Among the hydrocarbon radicals represented by R are alkyl radicals having from 1 to 18 carbon atoms, e.g., methyl, ethyl, propyl, butyl, octyl, dodecyl, octadecyl and the like; cycloalkyl radicals, e.g., cyclopentyl, cyclohexyl, cycloheptyl and the like; mononuclear and binuclear aryl radicals, e.g., phenyl, naphthyl and the like; aralkyl radicals, e.g., benzyl, phenylethyl, phenylpropyl, phenylbutyl and the like; alkaryl radicals, e.g., tolyl, xylyl, ethylphenyl and the like. Radicals represented by R" are alkylene radicals such as ethylene, propylene, butylene, pentamethylene, hexamethylene, octamethylene, dodecylmethylene, hexadecylmethylene and octadecylmethylene; arylene radicals such as phenylene, biphenylene and the corresponding alkylene and arylene radicals containing an oxygen atom. Other radicals represented by R" are vinylene, propenylene, butenylene and the like.

The epoxy-functional silanes represented above may contain monoepoxides and polyepoxides, particularly monoepoxides, diepoxides and triepoxides.

Examples of suitable silanes are gamma-glycidoxypropyltriethoxysilane, 4,5-epoxypentyltriethoxysilane, gamma-glycidoxypropyltripropoxysilane, gamma-glycidoxybutyltriethoxysilane, gamma-glycidoxypropyltributoxysilane, gamma-glycidoxypropyltrimethoxysilane, gamma-glycidoxyhexyltriethoxysilane, gamma-glycidoxyoctyltriethoxysilane, gamma-glycidoxyhexyltributoxysilane, glycidoxy-o,-phenyltriethoxysilane, 5,6-epoxyhexyltrimethoxysilane, 5,6-epoxyhexyltributoxysilane, 7,8-epoxyoctyltrimethoxysilane, 7,8-eposyoctyltripropoxysilane, 9,10-epoxydecyltrimethoxysilane, 9,10-epoxydecyltripropoxysilane, beta-3,4-(epoxycyclohexyl-ethyltrimethoxysiland and beta-3,4-(epoxycyclohexyl)-propyltributoxysilane.

Other epoxy-functional silanes which may be employed are those having the formula

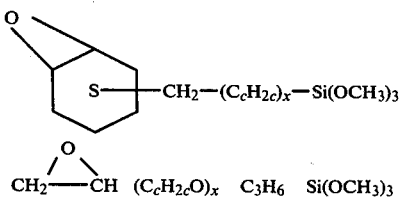

where c is a number of from 1 to 3 and x is a number of from 0 to 20.

These epoxy-functional silanes are mixed with cyclic organopolysiloxanes, and thereafter equilibrated in the presence of a base catalyst and preferably an aprotic solvent. The resulting epoxy or substituted epoxy-functional polysiloxane polymers may have a ratio of epoxy to siloxane units (R'$_2$SiO) of from 1 to 20,000.

The epoxy containing silanes employed in the equilibration may be prepared in accordance with the method described in U.S. Pat. No. 3,057,901 to Plueddemann. For example, epoxy containing silicon compounds may be prepared by the addition of an allyl glycidoxypropyl ether or butadiene monoepoxide to a compound containing SiH groups in the presence of a platinum catalyst at temperatures below 100° C.

Another method for preparing these epoxy containing silanes is to oxidize an unsaturated hydrocarbon substituent on a silicon with peracetic acid.

The cyclic siloxanes employed in the preparation of the polymers of this invention may be represented by the formula

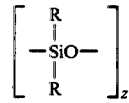

wherein R is the same as above and z is 3 to 6. These organopolysiloxanes can be hexamethylcyclotrisiloxane, hexaphenylcyclotrisiloxane, 1,2,3-trimethyl-1,2,3-triphenylcyclotrisiloxane, 1,2,3-trimethyl-1,2,3-trivinylcyclotrisiloxane, octamethylcyclotetrasiloxane, octaphenylcyclotetrasiloxane, decamethylcyclopentasiloxane and dodecamethylcyclohexasiloxane. It is preferred that an organocyclotrisiloxane be employed when lithium catalysts are used in the equilibration.

Examples of suitable catalysts are alkali metal alkoxides such as lithium methoxide, potassium methoxide, sodium methoxide, and lithium butoxides; alkali metal alkyls, e.g., ethyl lithium, ethyl potassium, ethyl sodium, isopropyl lithium, n-butyl lithium, vinyl lithium and the like; alkali aryls such as phenyl lithium, phenyl sodium and the like; alkali metal hydrides such as sodium, potassium and lithium hydride; alkali metal silanoates such as sodium, potassium and lithium silanoates, and hydroxides such as sodium, potassium, lithium and tetramethyl ammonium hydroxides.

The amount of catalyst is not critical, however, it is preferred that from 0.0001 mol percent to 1.0 mol percent of catalyst be employed to effect the reaction and that the mol ratio of catalyst to hydrocarbonoxy (OR) groups present in the epoxy-functional silane does not exceed about 1 to 12. However, it is recognized that greater amounts may be used, but it is the intent of this invention to provide a catalyst system which does not react with the reactive epoxy group.

In general, the equilibration can be carried out at temperatures ranging from about 25° C. up to about 150° C. or higher for times varying from a few minutes to several hours. Although it is not essential, it is preferred that the reaction be conducted in the presence of an inert atmosphere.

The reaction may be conducted in the absence or presence of a solvent. It is preferred that an aprotic solvent which is capable of coordinating with the cation be employed with lithium type catalysts. The term "aprotic solvent" is intended to mean any organic solvent that is free of active protons which will interfere with the growing anionic polymerization centers. These may include such solvents as various tertiary amines such as triethylamine, tributylamine, pyridine and the like. Other suitable solvents are dimethyl sulfoxide, dioxane, alkyl ethers; glycols such as diethylene glycol diethyl ether, dietylene glycol dimethyl ether, diethoxyethane, tetrahydrofuran and mixtures thereof. The use of mixtures of solvents having different boiling points permits this invention to be practiced at variable temperatures. However, it is preferred that certain special dipolar aprotic solvents having electron donating centers be employed. These solvents are chosen such that their electron donating centers are capable of forming coordination complexes with the cation, thereby coordinating with the cation and thus enhancing its reactivity by virtue of such coordination.

Certain other hydrocarbon solvents which do not coordinate with the cation can be employed with the aprotic solvents described above to provide more intimate contact between the reactants. Examples of suitable solvents are aliphatic hydrocarbons such as hexane, heptane, octane and aromatic hydrocarbons such as benzene, toluene, xylene and the like. It is preferred in the practice of this invention that from 0.05 to about 10 percent of the aprotic solvent having Lewis base characteristics be employed with lithium catalysts.

Generally, it is desirable to remove or destroy the catalysts after the equilibration because their presence will adversely affect the properties of the resulting polymers. The base catalysts, for example, may be removed by washing with water. Also, the base catalysts may be destroyed by neutralizing them with acid reagents, i.e., they may be neutralized by the addition of an acid. More specifically, the base type catalysts may be effectively neutralized by the addition of an organic acid such as acetic acid.

The epoxy-functional siloxane polymers of this invention may be used as intermediates in the preparation of copolymers containing organopolysiloxane segments which may be used in the formation of various coating compositions. In addition, these epoxy-functional siloxane polymers may be used as sizing agents and as protective coatings for paper and fabrics.

Various embodiments of this invention are illustrated in the following examples in which all parts are by weight unless otherwise specified.

EXAMPLE 1

A reaction vessel containing 222 parts of hexamethylcyclotrisiloxane, 200 parts of benzene and 22 parts of diethylene glycol dimethyl ether is heated to about 60° C. after which time about 23.6 parts of gamma-glycidoxypropyltrimethoxysilane and about 2 parts of n-hexane containing 15 weight percent of n-butyl lithium are added. The reaction mixture is heated to reflux temperature and maintained at this temperature for about 2.5 hours. The catalyst is neutralized by the addition of 0.5 parts of acetic acid and the reaction product filtered. The solvent is removed at 130° C. at 2 mm Hg over a period of about 4 hours. A clear fluid product is recovered. Nuclear magnetic resonance analysis of the product shows the following groups to be present in the indicated mol ratio:

| Groups | Actual | Theoretical |
| --- | --- | --- |
| CH$_2$—CH CH$_2$OC$_3$H$_6$Si—≡ (epoxy) | 0.32 | 0.33 |
| CH$_3$O— | 1.0 | 1.0 |
| (CH$_3$)$_2$SiO | 10.4 | 10.0 |

The resulting product has a viscosity of approximately 45 cs. at 25° C. and can be represented by the following structural formula

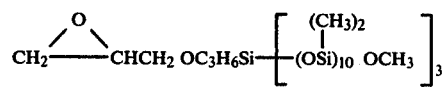

EXAMPLE 2

In a comparison example, the procedure of Example 1 is repeated except that gamma-glycidoxypropyltrimethoxysilane is omitted. The resulting product is a fluid having a viscosity of about 2200 cs. at 25° C. This example demonstrates that the molecular weight of the epoxy-functional siloxane is a function of the gamma-glycidoxypropyltrimethoxysilane.

EXAMPLE 3

A reaction vessel containing 222 parts of octamethylcyclotetrasiloxane, about 23.6 parts of gamma-glycidoxypropyltrimethoxysilane and about 0.2 part of potassium hydroxide are heated to about 145° C. and maintained at this temperature for about 2.5 hours. The catalyst is neutralized by the addition of 0.2 part of acetic acid and the reaction product filtered. The volatiles are removed at 130° C. at 2 mm Hg over a period of about 4 hours. A clear liquid product is recovered. Nuclear magnetic resonance analysis of the product shows the following groups to be present in the indicated mol ratio:

| Groups | Actual | Theoretical |
| --- | --- | --- |
| CH$_2$—CH CH$_2$OC$_3$H$_6$Si—≡ (epoxy) | 0.33 | 0.33 |
| CH$_3$O— | 1.0 | 1.0 |
| (CH$_3$)$_2$SiO | 10.2 | 10.0 |

The resulting product has a viscosity of approximately 55 cs. at 25° C. and can be represented by the following structural formula

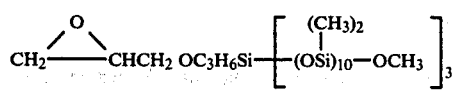

EXAMPLE 4

The procedure of Example 1 is repeated except that 133.2 parts of hexamethylcyclotrisiloxane, 13.3 parts of ethylene glycol dimethyl ether, 119.9 parts of benzene, 24.3 parts of gamma-glycidoxypropyltrimethoxysilane, and 0.064 part of n-butyl lithium are employed. A fluid having a viscosity of 23 cs. at 25° C. is obtained.

EXAMPLE 5

The procedure of Example 1 is repeated except that 24.7 parts of a silane of the formula

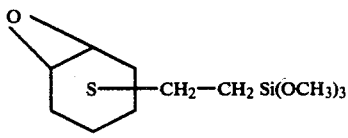

is substituted for the gamma-glycidoxypropyltrimethoxysilane. Analysis shows that the resultant product has the following formula

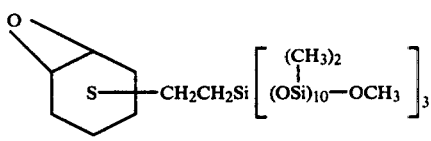

EXAMPLE 6

The procedure of Example 1 is repeated except that 37.6 parts of a silane of the formula

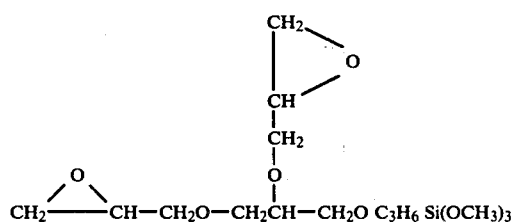

is substituted for the gamma-glycidoxypropyltrimethoxysilane. Analysis indicated that the resultant product has the following formula

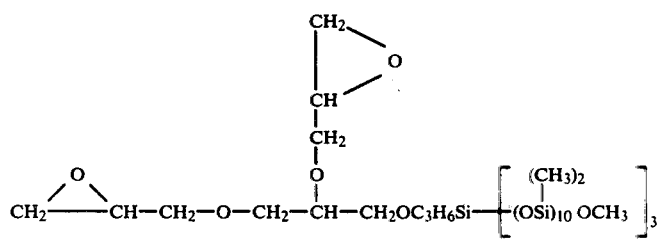

Although specific examples of the invention have been described herein, it is not intended to limit the invention solely thereto but to include all variations and modifications falling within the spirit and scope of the appended claims.

What is claimed is:

1. A composition comprising epoxy-functional polysiloxane polymers of the formula

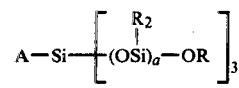

in which A is a radical containing at least one epoxy group, R is a monovalent hydrocarbon radical having up to 18 carbon atoms, and a is a number of from 1 to 20,000.

2. The composition of claim 1, wherein A is a radical of the formula

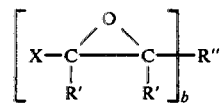

in which R' is selected from the class consisting of hydrogen and R, and when the R'(s) are taken together with the vicinal carbon atoms, may represent substituted and unsubstituted cyclic hydrocarbons, R" is selected from the class consisting of a divalent hydrocarbon radical, a trivalent hydrocarbon radical, tetravalent hydrocarbon radical, an oxyalkylene radical and oxyarylene radical having C—O—C linkages, X is selected from the class consisting of hydrogen and a monovalent hydrocarbon radical consisting of a single carbon atom or a group of carbon atoms interconnected by a single or multiple bond which contains additional groups selected from the class consisting of hydrogen, alkyl, hydroxyl, alkoxy and cyclic hydrocarbons, and b is a number of from 1 to 3.

3. The composition of claim 1, wherein R is a methyl radical.

4. The composition of claim 1, wherein the epoxy-functional polysiloxane has the formula

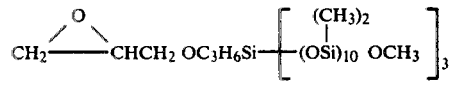

5. The composition of claim 1, wherein the epoxy-functional polysiloxane has the formula

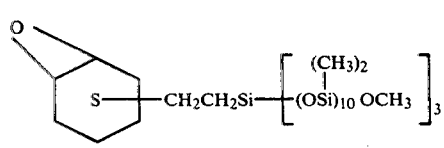

6. The composition of claim 1, wherein the epoxy-functional polysiloxane has the formula

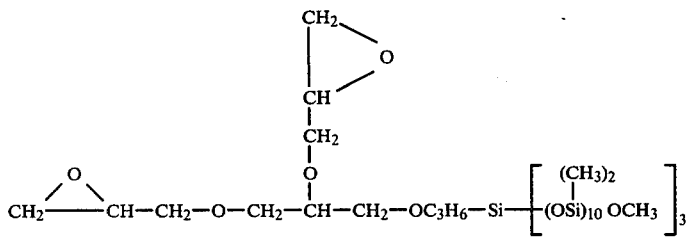

7. The composition of claim 2, wherein R' represents an alkyl radical.

8. The composition of claim 2, wherein X is hydrogen and the R'(s) together with the vicinal carbon atoms form a cyclic hydrocarbon.

9. The composition of claim 2, wherein R" is an alkylene radical.

10. The composition of claim 2, wherein R" is an oxyalkylene radical having C—O—C linkages.

11. A method for preparing the composition of claim 1, which comprises equilibrating in the presence of a basic catalyst selected from the group consisting of an alkali metal alkoxide, an alkali metal alkyl, an alkali metal hydride, an alkali metal silanoate, an alkali metal hydroxide and tetramethyl ammonium hydroxide and at an elevated temperature, a cyclic organopolysiloxane of the formula $$\left( \begin{array}{c} R \\ | \\ -SiO- \\ | \\ R \end{array} \right)_z$$

with a silane of the formula

A—Si(OR)$_3$ in which A is a radical having at least one epoxy group, R is a monovalent hydrocarbon radical having from 1 to 18 carbon atoms and z is from 3 to 6.

* * * * *